United States Patent
Zeng et al.

(10) Patent No.: US 9,976,113 B2
(45) Date of Patent: May 22, 2018

(54) METHODS, APPARATUSES, AND SYSTEMS FOR CELL AND TISSUE CULTURE

(71) Applicants: Agency for Science, Technology and Research, Singapore (SG); Carnegie Mellon University, Pittsburgh, PA (US)

(72) Inventors: Yukai Zeng, Singapore (SG); Philip R. Leduc, Pittsburgh, PA (US); Keng-Hwee Chiam, Singapore (SG)

(73) Assignees: Agency for Science, Technology and Research, Singapore (SG); Carnegie Mellon University, Pittsburgh, PA (US)

( * ) Notice: Subject to any disclaimer, the term of this patent is extended or adjusted under 35 U.S.C. 154(b) by 0 days. days.

(21) Appl. No.: 14/908,414

(22) PCT Filed: Aug. 7, 2014

(86) PCT No.: PCT/SG2014/000378
§ 371 (c)(1),
(2) Date: Jan. 28, 2016

(87) PCT Pub. No.: WO2015/020614
PCT Pub. Date: Feb. 12, 2015

(65) Prior Publication Data
US 2016/0160165 A1    Jun. 9, 2016

Related U.S. Application Data
(60) Provisional application No. 61/958,843, filed on Aug. 7, 2013.

(51) Int. Cl.
    *C12M 3/00*     (2006.01)
    *C12M 1/00*     (2006.01)
    (Continued)

(52) U.S. Cl.
CPC .......... *C12M 23/20* (2013.01); *C12M 23/12* (2013.01); *C12M 23/44* (2013.01); *C12M 25/04* (2013.01); *C12M 25/06* (2013.01); *C12M 35/04* (2013.01)

(58) Field of Classification Search
CPC ...... C12M 23/12; C12M 23/20; C12M 23/26; C12M 23/44; C12M 25/04; C12M 25/06; C12M 35/04
See application file for complete search history.

(56) References Cited

U.S. PATENT DOCUMENTS

| 4,299,920 A | * | 11/1981 | Peters | C12M 23/12 435/288.4 |
| 5,554,536 A | * | 9/1996 | Rising | B01L 3/50255 422/561 |

(Continued)

FOREIGN PATENT DOCUMENTS

| WO | WO-88/00235 A1 | 1/1988 | |
| WO | WO 2009032164 A1 * | 3/2009 | ............ C12M 23/12 |

(Continued)

OTHER PUBLICATIONS

Zeng, Y. et al., Investigating Circular Dorsal Ruffles through Varying Substrate Stiffness and Mathematical Modeling, Biophysical Journal, 101(9), 2122-2130 (2011).

(Continued)

*Primary Examiner* — William H. Beisner
(74) *Attorney, Agent, or Firm* — Choate, Hall & Stewart LLP

(57) ABSTRACT

This invention provides an apparatus and method for culturing cells to probe the influence that the properties of a surface onto which the cells are bonded has on the properties of the cell.

25 Claims, 8 Drawing Sheets

(51) Int. Cl.
*C12M 1/32* (2006.01)
*C12M 1/12* (2006.01)
*C12M 1/42* (2006.01)

(56) References Cited

U.S. PATENT DOCUMENTS

| | | | |
|---|---|---|---|
| 6,814,966 B1* | 11/2004 | Wax | A61K 31/00 |
| | | | 424/130.1 |
| 6,908,760 B2* | 6/2005 | Cima | B01L 3/5088 |
| | | | 435/288.4 |
| 2004/0087007 A1* | 5/2004 | Cima | G01N 33/5008 |
| | | | 435/287.1 |
| 2010/0190249 A1 | 7/2010 | Kruse et al. | |
| 2010/0216242 A1 | 8/2010 | Shimizu et al. | |
| 2012/0295299 A1* | 11/2012 | Gazenko | C12M 23/10 |
| | | | 435/34 |

FOREIGN PATENT DOCUMENTS

| | | |
|---|---|---|
| WO | WO-2010/124207 A1 | 10/2010 |
| WO | WO-2012/040579 A2 | 3/2012 |
| WO | WO-2013/074972 A1 | 5/2013 |

OTHER PUBLICATIONS

International Search Report for PCT/SG2014/000378, 4 pages (dated Nov. 12, 2014).

Written Opinion for PCT/SG2014/000378, 5 pages (dated Nov. 12, 2014).

Discher, D.E. et al., Tissue Cells Feel and Respond to the Stiffness of Their Substrate, Science, American Association for the Advancement of Science, 310(5751): 1139-1143 (2005).

Phelham, R.J. et al., Cell locomotion and focal adhesions are regulated by substrate flexibility, Proceedings of the National Academy of Sciences, 94(25): 13661-13665 (1997).

* cited by examiner

METHODS, APPARATUSES, AND SYSTEMS FOR CELL AND TISSUE CULTURE

CROSS-REFERENCE TO RELATED APPLICATIONS

This patent application is a National Stage Entry of International Patent Application No. PCT/SG2014/000378, filed on Aug. 7, 2014, which claims the benefit under 35 U.S.C. § 119(e) of U.S. provisional application Ser. No. 61/958,843 filed on 7 Aug. 2013, the contents of which are herein incorporated by reference in their entirety.

FIELD OF THE INVENTION

This invention relates to an apparatus and methods for cell and tissue culture. More specifically, this invention relates to a cell culture apparatus that provides dynamic and reversible control of local substrate elasticity in devices used for in vitro cell and tissue culture.

BACKGROUND OF THE INVENTION

The fabrication of cell culture substrates in 2-D with tunable stiffnesses has been an intensively studied field in mechanobiology. Previous studies have revealed that cell motility, the reorganization of cellular cytoskeleton and stem cell differentiation are influenced by substrate stiffness and compliance.

Polymeric substrates which have been used in extracellular substrate stiffness studies include poly(ethylene glycol) (PEG) gels, polydimethylsiloxane (PDMS), polyacrylamide (PA) and hyaluronic acid (HA) based polymer systems. These polymers require the establishment of unique formulations for each gel system, such as tuning the different cross-linker concentrations to vary the stiffness of the gel system. A major disadvantage and limitation of these systems are that the material properties are fixed and not dynamic. As such, spatially dynamic stiffness gradients within hydrogels have been formulated to overcome these limitations. For example, hydrogels with differing stiffnesses on the same substrate have been fabricated by mixing different formulations of PA gels. More advanced fabrication techniques have made use of microfluidics to fabricate PA gel gradients. PDMS substrates with stiffness gradients have also been fabricated from patterning. Although substrate stiffness properties can be dynamically controlled spatially in these cases, the limitation of static temporal stiffness in these systems still exists.

To overcome the limitation in temporal stiffness experienced by existing polymeric systems, ultra-violet (UV) photomodulatable hydrogels have been used, such as PA, PEG and methacrylated HA. However, these systems still face a limitation as the change in stiffness is not reversible spatially or temporally. The stiffness of the substrates can only soften or stiffen with time.

Present methods to fabricate thin-film polymers include the spin coating of PDMS as well as the fabrication of thin PDMS films from silicon wafer molds. Disadvantages to current thin-film fabrication methods are that the direct spin coating or pouring of PDMS into molds would cause the PDMS to stick to the underlying substrate, and the PDMS thin-film is subjected to a large peeling force when the film is removed from the substrate, possibly tearing it. Even if the films are able to be removed, the lateral dimensions of the films are limited to hundreds of microns in length.

In addition, current existing methods for fabricating bilayer polymeric substrates suitable for 2-D cell culture include polyelectrolyte multilayer (PEM) fabrication by depositing polyanions and polycations separately onto a surface and the successive spin coating of polymers on top of one another on a rigid substrate. Such methods do not allow the separation of the individual layers away from the bilayer structure.

Of the known apparatus and systems mentioned above, none can be used to induce different cell growth characteristics (i.e. such as morphology, motility, aggregation, differentiation etc.) in a reversible manner such that the induction of different growth characteristics can be dynamically changed and selected.

There is therefore a need to provide an apparatus or method that at least partially ameliorates one or more of the disadvantages described above.

SUMMARY OF THE INVENTION

A cell culture apparatus for culturing cells, the apparatus comprising at least one chamber for containing and growing the cells therein, the chamber being adapted to connect with at least one removable member of a set of removable members, each of the removable members of said set providing a surface for cell adhesion and having a different stiffness relative to other removable members of the set, the stiffness of each removable member of said set being selected to induce cell growth that is different from other removable members within the set.

Advantageously, the cell culture apparatus provides a cell culture environment for cells that enables the cells to be exposed to growth surfaces with varying stiffness both spatially and temporally. That is, the cells can be exposed to growth surfaces with different stiffnesses simultaneously or over a period of time. Advantageously, the apparatus is adapted to enable reversible spatial and temporal change in stiffness of the growth surface. That is, the cells may first be exposed to a surface having stiffness A, then subsequently to a surface having stiffness B after a certain period of time, then back to a surface having stiffness A after another period of time. Alternatively, the cells may be exposed to a surface having stiffness A, then a surface having stiffness B, then a surface having stiffness C, over a period of time. Alternatively again, the cells may simultaneously be exposed to growth surfaces having multiple stiffness. Advantageously, due to the way the apparatus is configured, the cells may be exposed to different growth surface stiffnesses without having to be removed from the growth surface. As such, it is possible to monitor the cell property when the cells are exposed to different stiffness growth surfaces without imparting any physical or biochemical stress to the cells that may occur during cell removal from a surface.

Advantageously, the apparatus is adapted such that the cells are grown within a chamber which can be connected and disconnected to a removable member. The removable member may be one of a set of removable members that may have a selected stiffness that is different to the stiffness of other removable members in the set. The chamber may comprise a containment layer or a membrane to which the cells may adhere thereon. The containment layer or membrane may have a selected dimension or thickness that may allow the cells to be affected by or sense the environment on the other side of the containment layer or membrane. Advantageously, cells are able to sense the thickness of substrates that they are being seeded on, as has been quantified by traction forces in 3-dimensions. As such, the cells may be affected or sense the stiffness of the substrate to which the surface it is adhered thereon is exposed to.

As the chamber can be connected and disconnected from the removable member, changing of the stiffness of the removable member enables the cells that are adhered to the containment layer or membrane to be affected by or sense the stiffness of the removable member through the containment layer or the membrane. As such, by connecting different removable members with a different selected stiffness, it enables the cells to be affected by or to sense the stiffness of the respective removable members, consequently experiencing different growth surface stiffness.

Advantageously, this apparatus may be used as a tool to investigate the influence of reversible dynamic stiffness environments on cell morphology, motility, proliferation and differentiation in various cells types.

A method for culturing cells in a cell culture apparatus, the method comprising the step of incubating cells while exposed to a set of surfaces for cell adhesion, wherein each surface of the set has a different stiffness to other surfaces within the set, wherein the stiffness of each surface is selected to induce cell growth that is different from other surfaces within the set.

Advantageously, the method allows induction of different cell growth characteristics (i.e. such as morphology, motility, aggregation, differentiation etc.) in a reversible manner such that the induction of different growth characteristics can be dynamically changed and selected.

A cell culture kit for culturing cells having different growth characteristics, the kit comprising: at least one chamber for containing and growing the cells therein and containing at least one receiving conduit for being coupled to a removable members that contains surface of growing cells thereon; a set of removable members that are configured to couple to receiving conduit of the chamber, each of said removable members having a selected stiffness that is different to other removable members of the set, the stiffness of each member being selected to induce cell growth that is different from other removable members within the set Definitions The following words and terms used herein shall have the meaning indicated:

The term "stiffness", for the purposes of this application, refers to the rigidity of an object and is a measure to which an object resists deformation in response to an applied force. The stiffness may be measured with a single degree of freedom or with multiple degrees of freedom. For the purposes of this application, the elastic modulus may also be considered to be a measure of stiffness. Other measures of stiffness may include rotational modulus, bulk modulus, shear modulus and any combination thereof.

The term "cell growth", for the purposes of this application, refers to any process during cell development and cell division. Cell growth may include cell size growth or increase of cell number. More specifically, it may include cell adherence, spreading, aggregation, migration, proliferation, differentiation, function or combinations thereof.

The word "chamber" in the context of this specification refers to any enclosed space that is capable of supporting materials for cell growth. The chamber may be an "open" chamber in which in use the enclosed space has at least one conduit that is not enclosed. The chamber may also be a "closed" chamber in use, which means that there are no conduits to an external environment when the chamber is in use. The chamber can be any shape or dimension but in a preferred embodiment, the chamber is cylindrically shaped and in another the chamber is prism shaped.

The term "cylinder", for the purposes of this disclosure, may be a 3-dimensional shape formed by the points at a fixed distance from a given line segment that is the axis of the cylinder, and two planes (base faces) perpendicular to this axis. All cross-sections parallel to the base faces may be the same. The cross-section may be a circle, ellipse, parabola or hyperbola. The cylinder may be a right circle cylinder, elliptic cylinder, parabolic cylinder or hyperbolic cylinder.

The term "prism", for the purposes of this disclosure, may be a 3-dimensional shape formed by an n-sided polygonal base, a translated copy (not in the same plane as the first) and n other faces joining the corresponding sides of the two bases. The prism may be a right prism in which the joining edges and faces are perpendicular to the base faces. The prism may be an oblique prism where the joining edges and the faces are not perpendicular to the base faces. All cross-sections parallel to the base faces may be the same. The cross-section may be a polygon. The polygon may be any n-gon. The polygon may be a triangle, quadrilateral, pentagon, hexagon, heptagon, octagon, nonagon, decagon, hendecagon, dodecagon, pentadecagon, icosagon, hectagon, chiliagon, myriagon or megagon.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the terms "about" and "approximately", in the context of concentrations of components of the formulations, or where applicable, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DISCLOSURE OF OPTIONAL EMBODIMENTS

A cell culture apparatus for culturing cells may comprise at least one chamber for containing and growing the cells therein, the chamber being adapted to connect with at least one removable member of a set of removable members, each of the removable members of said set providing a surface for cell adhesion and having a different stiffness relative to other removable members of the set, the stiffness of each removable member of said set being selected to induce cell growth that is different from other removable members within the set.

The chamber may be adapted to connect with at least one removable member of a set of removable members. The connection between the chamber and the at least one removable member may be reversible. That is, the chamber may be disconnected from the at least one removable member. The chamber may be connected to a single removable member. The chamber may be simultaneously connected to two or more removable members.

The chamber may be closed or open. A closed chamber may comprise a horizontal base and a horizontal lid that are parallel to each other, and at least one side that is perpendicular to both the base and lid. An open chamber may comprise of a horizontal base and at least one side that is perpendicular to the base. The at least one side of the chamber may be the sidewalls of the chamber.

The base of the chamber may be a circle, ellipse or any polygon shape. The polygon may be any regular n-gon that is equiangular and equilateral. The polygon may be an equilateral triangle, square, regular pentagon, regular hexagon, regular heptagon, regular octagon, regular nonagon, regular decagon, regular hendecagon, regular dodecagon, regular pentadecagon, regular icosagon, regular hectagon, regular chiliagon, regular myriagon or regular megagon.

The side of the chamber may be continuous if the base is a circle of an ellipse. There may be as many sides as the sides of the polygon if the base of the chamber is a polygon shape.

The chamber may have a 3-dimensional shape that is a cylinder or prism.

The apparatus may comprise a removable lid to enclose the chamber. The removable lid may have the same shape as the base of the chamber. The removable lid may enable the chamber to be completely enclosed. The enclosed chamber with the lid may not allow diffusion of gases or liquids between the inside of the enclosed chamber and the outside of the enclosed chamber. The enclosed chamber with the lid may allow some diffusion of gases or liquids. The enclosed chamber with the lid may allow exchange of atmospheric gases such as oxygen, nitrogen, argon, carbon dioxide, water vapour or any mixture thereof, between the inside of the chamber and the outside of the chamber.

The chamber may comprise a surface in contact with cells during cell culture. The surface in contact with the cells may be the base, lid or at least one side of the chamber. The surface in contact with the cells may be the base of the chamber.

The apparatus may comprise at least one containment layer for containing cells within the chamber during cell culture, the containment layer disposed between the interior of the chamber and the surface for cell adhesion of the removable member connected to the chamber.

The apparatus may comprise at least one containment layer for containing cells within the chamber during, cell culture, the containment layer being capable of being coupled to the chamber and partially disposed on the at least one removable member when connected to the chamber.

The containment layer may be the surface in contact with cells during cell culture. The containment layer may be the base of the chamber.

The containment layer may be dimensioned to enable cell growth to be affected by the surface for cell adhesion of the removable member. The surface for cell adhesion of the removable member may affect cell adherence, spreading, growth, aggregation, migration, proliferation, differentiation, function or combinations thereof that is different from other removable members within the set.

The properties of the cell that may affected by the surface for cell adhesion of the removable member may be morphology, biochemistry, adhesion strength, growth rate, aggregation rate, motility migration rate, proliferation rate, differentiation rate or combinations thereof.

The apparatus may comprise a polymer membrane. The chamber may comprise a polymer membrane. The containment layer may comprise a polymer membrane. The base, lid or combinations thereof of the containment layer may comprise a polymer membrane. The base of the containment layer may comprise a polymer membrane. The surface in contact with the cells may be the polymer membrane. The surface in contact with the cells may be a surface of the polymer membrane. The polymer membrane may have a first surface and a second surface. The surface in contact with the cells may be the first surface of the polymer membrane.

The polymer membrane may comprise a polymer sheet disposed between sidewalls of the chamber and the surface for cell adhesion of the removable member. The polymer sheet may act as a barrier between the contents of the chamber and the removable member.

The polymer of the polymer membrane may be any polymer onto which a cell may adhere, spread, grow, aggregate, migrate or combinations thereof. The polymer may be a synthetic polymer, naturally-occurring polymer or any mixture thereof. The polymer may be a copolymer. The polymer may be biodegradable.

The polymer of the polymer membrane may be selected from the group consisting of polydimethylsiloxane, polyacrylamide, polyethylene glycol, hyaluronic acid, polystyrene, poly(hydroxyethylmethacrylate), polycaprolactone, polylactic acid, poly(methylmethacrylate), polyacrylonitrile, polyamide and any mixture thereof.

The polymer of the polymer membrane may comprise an additive that may alter the physical or chemical properties of the polymer membrane.

The additive of the polymer of the polymer membrane may be selected from the group consisting of dielectric gel, elastomer, curing agent, solvent, pigment, stabilizer, UV stabilizer, heat stabilizer, biostabilizer, antioxidant, surfactant, plasticizer, lubricant, anti-counterfeit, antimicrobial, antistatic agent, blowing agent, filler, extender, flame retardant, process aid, reinforcement and any combination thereof.

The additive of the polymer of the polymer membrane may confer stiffness to the polymer substrate. The additive of the polymer of the polymer membrane may be selected to modulate the stiffness of the polymer of the polymer membrane.

The polymer of the polymer membrane may comprise the polymer and a curing agent in a ratio in the range of about 30:1 to about 5:1, about 30:1 to about 20:1, about 30:1 to about 10:1, about 20:1 to about 10:1, about 20:1 to about 5:1 or about 10:1 to about 5:1.

The containment layer may be dimensioned to enable cell growth to be affected by the surface for cell adhesion of the removable member. The dimension may be thickness. The containment layer may be dimensioned to enable cell growth to be affected by the surface for cell adhesion of the removable member. The polymer membrane may have a thickness to enable cell growth to be affected by the surface for cell adhesion of the removable member. The polymer sheet may have a thickness to enable cell growth to be affected by the surface for cell adhesion of the removable member.

The surface for cell adhesion of each removable member may have a different stiffness relative to other removable members of the set. The stiffness of a removable member may be selected to induced cell growth that is different from other removable members within the set. The containment layer may have a thickness that allows the cells adhered thereon to be cultured based on the stiffness of the at least one removable member onto which it is disposed. The polymer membrane may have a thickness that allows the cells adhered thereon to be cultured based on the stiffness of the at least one removable member onto which it is disposed. The polymer sheet may have a thickness that allows the cells adhered thereon to be cultured based on the stiffness of the at least one removable member onto which it is disposed.

The polymer membrane may have a thickness in the range of about 50 nm to about 5 µm, about 50 nm to about 75 nm, about 50 nm to about 100 nm, about 50 nm to about 200 nm, about 50 nm to about 500 nm, about 50 nm to about 1 µm, about 50 nm to about 2 µm, about 50 nm to about 5 µm, about 75 nm to about 100 nm, about 75 nm to about 200 nm, about 100 nm to about 500 nm, about 100 nm to about 1 µm, about 100 nm to about 2 µm, about 100 nm to about 5 µm, about 200 nm to about 500 nm, about 200 nm to about 1 µm, about 200 nm to about 2 µm, about 200 nm to about 5 µm, about 500 nm to about 1 µm, about 500 nm to about 2 µm, about 500 nm to about 5 µm, about 1 µm to about 2 µm, about 1 µm to about 5 µm or about 2 µm to about 5 µm.

The polymer membrane may be coated with a coating. The coating may be any coating that modulates cell adherence, spreading, growth, aggregation, migration, differentiation, proliferation, function or combinations thereof. The coating may be a coating that is hydrophilic, hydrophobic, ionic or combinations thereof. The coating may comprise an amino acid, protein, polymer or any mixture thereof. The coating may be any compound that is a component of the extracellular matrix. The coating may be poly-L-lysine, fibronectin, collagen I, collagen IV, or any combination thereof.

The chamber may comprise at least one cell. The cell may be any cell of any organism. The organism may be a vertebrate, insect, plant or bacterium. The cell may be a primary cell, a cell line or genetically modified cell. The containment layer may comprise a single cell type or a mixture of different cell types.

The chamber may comprise a gas or liquid. The gas may be atmospheric air. The gas may be any gas suitable for culturing cells. The gas may comprise 5% $CO_2$ and 95% air. The liquid may be any liquid that enables survival of cells. The liquid may be water, solution, buffer, cell culture media or any mixture thereof.

The chamber may be adapted to connect with at least one removable member of a set of removable members to provide a surface for cell adhesion thereon. The chamber may be adapted to connect with a single removable member of a set of removable members to provide a surface for cell adhesion thereon. The chamber may be adapted to connect with plural removable members of a set of removable members to provide a surface for cell adhesion thereon.

A set of removable members may comprise at least one removable member. A set of removable members may comprise two or more removable members. A set of removable members may comprise about 1 to about 10 removable members.

Each of the removable member in a set of removable members may have a different stiffness relative to other removable members of the set.

The stiffness of a removable member may be selected to induce cell adherence, spreading, growth, aggregation, migration, proliferation, differentiation, function or combinations thereof that is different from other removable members within the set.

The stiffness of a removable member may be selected to induce cell growth that is different from other removable members within the set.

The cell adherence, spreading, growth, aggregation, migration, differentiation, proliferation, function or combinations thereof may be depending on the stiffness of the surface onto which the cell is in contact with.

The properties of the cell that may change or be different depending on the stiffness of the surface onto which it is in contact with may be morphology, biochemistry, adhesion strength, growth rate, motility, aggregation rate, migration rate, differentiation rate, proliferation rate or combinations thereof.

Each removable member may independently comprise a substrate with a selected stiffness. The substrate may be any material that has a suitable stiffness for culturing cells thereon. The substrate may be a solid, liquid, gas or gel. The substrate may comprise a polymer, metal, wood or any thereof.

Each removable member may independently comprise a polymer substrate. Each removable member may independently comprise a polymer substrate with a selected stiffness.

The stiffness of the polymer substrate may be in the range of about 1 to about 2000 kPa.

The polymer of the polymer substrate may be selected from the group consisting of polydimethylsiloxane, polyacrylamide, polyethylene glycol, hyaluronic acid, poly(hydroxyethylmethacrylate), polyethylene glycol, polycaprolactone, polylactic acid, poly(methylmethacrylate), polyacrylonitrile, polyamide, agar, agarose, collagen and any mixture thereof.

The polymer of the polymer substrate may comprise an additive.

The additive may be any material that chemically or physically changes the property of the polymer.

The set of polymer substrates have different stiffness to each other due to additives that confer stiffness on the polymer substrates and in which each polymer substrate of the set has different levels of additives contained therein.

The additive that confers stiffness to the polymer substrate may be selected from the group consisting of dielectric gel, elastomer, curing agent, solvent, pigment, stabilizer, UV stabilizer, heat stabilizer, biostabilizer, antioxidant, surfactant, plasticizer, lubricant, anti-counterfeit, antimicrobial, antistatic agent, blowing agent, filler, extender, flame retardant, process aid, reinforcement and any combination thereof.

The additive may be selected to modulate the stiffness of the polymer of the polymer substrate.

The additive for the polymer of the polymer substrate may be selected from the group consisting of dielectric gel, elastomer, curing agent, solvent and any combination thereof.

The polymer of the polymer substrate may comprise a dielectric gel and an elastomer in a ratio in the range of about 2:1 to about 1:1, about 2:1 to about 1:2, about 2:1 to about 1:5, about 2:1 to about 1:10, about 2:1 to about 1:20, about 1:1 to about 1:2, about 1:1 to about 1:5, about 1:1 to about 1:10, about 1:1 to about 1:20, about 1:2 to about 1:5, about 1:2 to about 1:10, about 1:2 to about 1:20, about 1:5 to about 1:10, about 1:5 to about 1:20 or about 1:10 to about 1:20.

The containment layer may be at least partially disposed on at least one removable member. The containment layer may be completely disposed on a single removable member. The containment layer may be partially disposed on a single removable member. The containment layer may be simultaneously and completely disposed on two or more removable members. The containment layer may be simultaneously and partially disposed on two or more removable members.

The containment layer may comprise a polymer membrane. The polymer membrane may have a first surface and a second surface. The first surface of the polymer membrane may be in contact with the cells. The second surface of the polymer membrane may at least be partially disposed on at least one removable member. The containment layer may be The apparatus may comprise a liquid layer disposed on the at least one removable member selected to reduce adhesion of the removable member to the chamber. The reduction in adhesion may aid in separation between the removable member and the chamber when disconnecting the chamber from the removable member.

The liquid layer may be disposed in between the at least one removable member and the chamber. The liquid layer may be disposed in between the at least one removable member and the at least one containment layer. The liquid layer may comprise any liquid that may reduce adhesion forces between the removable member and the chamber or containment layer. The liquid may be water, solution, buffer, or any mixture thereof. The solution may be a solution of sucrose, poly(acrylic acid), dextran, poly(methylacrylic acid), poly(acrylamide), poly(ethylene oxide) or any variant thereof, or any mixture thereof.

The apparatus may comprise at least one chamber. The apparatus may comprise a single chamber. The apparatus may comprise two or more chambers. The apparatus may comprise plural chambers. The apparatus may comprise about 1 to about 400 containment layers. The apparatus may comprise about 1, about 4, about 6, about 8, about 12, about 24, about 48, about 96, about 192, about 288 or about 384 chambers.

The apparatus may comprise multiple removable members configured to interact with multiple chambers so that cells contained within the containment layer of each chamber are able to be contacted with the multiple removable members during cell growth.

A method for culturing cells in a cell culture apparatus may comprise the step of incubating cells while exposed to a set of surfaces for cell adhesion, wherein each surface of the set has a different stiffness to other surfaces within the set, wherein the stiffness of each surface is selected to induce cell growth that is different from other surfaces within the set.

The method for culturing cells may comprising the step of contacting cells with the at least one chamber.

The method for culturing cells may comprise the step of incubating the cells in contact with the chamber.

The incubation step may be performed for a duration of time that is sufficient to enable cell growth to be affected by the surface for cell adhesion of the removable member.

The incubating step may be performed for a duration of time in the range of about 1 minute to about 72 hours, about 1 minute to about 20 minutes, about 1 minute to about 40 minutes, about 1 minute to about 1 hour, about 20 minutes to about 40 minutes, about 20 minutes to about 1 hour, about 1 hour to about 2 hours, about 1 hour to about 4 hours, about 1 hour to about 6 hours, about 1 hour to about 8 hours, about 1 hour to about 10 hours, about 2 hours to about 4 hours, about 2 hours to about 6 hours, about 2 hours to about 8 hours about 2 hours to about 10 hours, about 4 hours to about 6 hours, about 4 hours to about 8 hours about 4 hours to about 10 hours, about 6 hours to about 8 hours, about 6 hours to about 10 hours, about 8 hours to about 10 hours, about 10 hours to 24 hours, about 10 hours to 48 hours, about 10 hours to 72 hours, about 24 hours to 48 hours, about 24 hours to 72 hours or about 48 hours to about 72 hours.

The incubating step may be performed in standard cell culture conditions known to a person skilled in the art. Standard cell culture conditions may comprise an ambient temperature in the range of 35° C. to 38° C., ambient atmosphere, $CO_2$-enriched atmosphere or combinations thereof.

The method may comprise the step of consecutively exposing the cells to the set of surfaces for cell adhesion. The method may comprise the step of simultaneously exposing the cells to the set of surfaces for cell adhesion.

The method may comprise the step of providing at least one chamber for containing and growing the cells therein, the chamber being adapted to connect with at least one removable member of a set of removable members, each removable member having the surface for cell adhesion thereon.

The method may comprise the step of separating the cells from the surface for growing the cells using a containment layer therebetween. The separating step may be performed by providing a containment layer. The containment layer may be a membrane for the cells to grow thereon.

The method for culturing cells may comprise the step of connecting the at least one chamber with the at least one removable member.

The method may comprise the step of removing the at least one removable member.

The method may comprise the step of reconnecting the chamber with a different removable member in the set of removable members.

The method may comprise the step of reincubating the cells in contact with the chamber.

The reincubation step may be performed for a duration of time that is sufficient to enable cell growth to be affected by the surface for cell adhesion of the removable member.

The reincubation step may be performed for a duration of time in the range of about 1 minute to about 72 hours, about 1 minute to about 20 minutes, about 1 minute to about 40 minutes, about 1 minute to about 1 hour, about 20 minutes to about 40 minutes, about 20 minutes to about 1 hour, about 1 hour to about 2 hours, about 1 hour to about 4 hours, about 1 hour to about 6 hours, about 1 hour to about 8 hours, about 1 hour to about 10 hours, about 2 hours to about 4 hours, about 2 hours to about 6 hours, about 2 hours to about 8 hours about 2 hours to about 10 hours, about 4 hours to about 6 hours, about 4 hours to about 8 hours about 4 hours to about 10 hours, about 6 hours to about 8 hours, about 6 hours to about 10 hours, about 8 hours to about 10 hours, about 10 hours to 24 hours, about 10 hours to 48 hours, about 10 hours to 72 hours, about 24 hours to 48 hours, about 24 hours to 72 hours or about 48 hours to about 72 hours.

A cell culture kit for culturing cells having different growth characteristics may comprise at least one chamber for containing and growing the cells therein and containing at least one receiving conduit for being coupled to a removable members that contains surface of growing cells thereon; a set of removable members that are configured to couple to receiving conduit of the chamber, each of said removable members having a selected stiffness that is different to other removable members of the set, the stiffness of each member being selected to induce cell growth that is different from other removable members within the set.

A method for fabricating a cell culture apparatus for culturing cells, the method comprising the steps of: providing at least one chamber for containing and growing the cells therein; providing at least one removable member of a set of removable members having a surface for cell adhesion and having a different stiffness relative to other removable members of the set; and connecting the chamber with at least one removable member having a selected stiffness, the stiffness being selected to induce cell growth that is different from other removable members within the set.

The method for fabrication may comprise at least one containment layer for containing cells within the chamber during cell culture, the containment layer being capable of being coupled to the chamber and partially disposed on the at least one removable member when connected to the chamber.

The method for fabrication may comprise the step of dimensioning the containment layer to enable cell growth to be affected by the surface for cell adhesion of the removable member.

The method for fabrication may comprise the step of disposing the polymer membrane between sidewalls of the chamber and the surface for cell adhesion of the removable member.

The step of providing at least one chamber may comprise the step of forming the polymer membrane and attaching an upright frame to the polymer membrane to form the chamber.

The step of forming the polymer membrane may be performed by any technique known in the art for obtaining a thin layer of chemicals or polymers. The step of forming the polymer membrane may comprise coating a silicon wafer with a sacrificial layer. The sacrificial layer may be any chemical or solvent that may form a thin layer that reduces adhesion between the silicon wafer and the membrane. The sacrificial layer may comprise a liquid selected from the group consisting of photoresist, SU-8, sucrose solution, 5% (w/v) sucrose solution, poly(acrylic acid), poly(methyacrylic acid) and dextran solutions. The solvent for the sacrificial layer may be selected from the group consisting of SU-8 developer solution, organic solvents and water.

The coating may be done by spin-coating, layer-by-layer deposition, chemical solution deposition, chemical vapour deposition, physical deposition using mechanical, thermodynamic and electromechanical methods or combinations thereof.

The step of forming the polymer membrane may comprise the step of mixing the polymer of the membrane polymer with at least one additive. The additive may be a curing agent. The polymer of the polymer membrane may be mixed with a curing agent in a ratio in the range of about 30:1 to about 5:1, about 30:1 to about 20:1, about 30:1 to about 10:1, about 20:1 to about 10:1, about 20:1 to about 5:1 or about 10:1 to about 5:1.

The step of forming the polymer membrane may comprise the step of diluting the mixture of the polymer and curing agent with a solvent. The solvent may be an organic solvent. The solvent may be hexane, methanol, ethanol, acetone, ethyl acetate, chloroform, dichloromethane or any mixture thereof. The mixture of the polymer and curing agent may be diluted with a solvent in a ratio in the range of about 1:2 to about 1:100, about 1:2 to about 1:5, about 1:2 to about 1:10, about 1:2 to about 1:20, about 1:2 to about 1:30, about 1:2 to about 1:60, about 1:2 to about 1:90, about 1:5 to about 1:10, about 1:5 to about 1:20, about 1:5 to about 1:30, about 1:5 to about 1:60, about 1:5 to about 1:90, about 1:10 to about 1:20, about 1:10 to about 1:30, about 1:10 to about 1:60, about 1:10 to about 1:90, about 1:20 to about 1:30, about 1:20 to about 1:60, about 1:20 to about 1:90, about 1:30 to about 1:60, about 1:30 to about 1:90 or about 1:60 to about 1:90.

The step of forming the polymer membrane may comprise the step of depositing a layer of the polymer, polymer mixed with an additive or diluted mixture of polymer and additive onto the silicon wafer that has been optionally coated with photoresist. The depositing may be performed by any technique known in the art for obtaining a thin layer of chemicals or polymers. The coating may be performed by spin-coating. The spin-coating may be performed at a rotational speed in the range of 5000 RMP to 8000 RPM for a duration in the range of 100 seconds to 200 seconds.

The step of providing at least one chamber may comprise the step of heating the polymer, polymer mixed with an additive or diluted mixture of polymer and additive that has been deposited onto the silicon wafer optionally coated with photoresist.

The providing at least one chamber may comprise the step of attaching at least one upright frame to the polymer membrane to form at least one chamber. The upright frame may comprise a lid, at least one side, or combinations thereof. The upright frame may comprise sidewalls of the chamber.

The upright frame may comprise a polymer. The polymer of the upright frame may be selected from the group consisting of polydimethylsiloxane, polystyrene, polycarbonate, polypropylene, polyethylene, polyvinyl chloride and any mixture thereof.

The upright frame may be bonded to the polymer membrane. The bonding may be performed by thermal adhesion. The thermal adhesion may be performed if the upright frame has a similar surface chemistry to the polymer membrane. Thermal adhesion may be performed by contacting the upright frame with the polymer membrane before the upright frame has not fully cured. The bonding may be performed by use of an external adhesive. An external adhesive may be used if the surface chemistry of the upright frame and the polymer membrane do not have similar surface chemistry. The external adhesive may be an epoxy-based glue, a UV-adhesive glue or any combination thereof.

The method may comprise the step of providing at least one removable member of a set of removable members having a surface for cell adhesion and having a different stiffness relative to other removable members of the set.

Each of the removable member in a set of removable members may be selected to have a different stiffness relative to other removable members of the set.

The stiffness of a removable member may be selected to induce cell adherence, spreading, growth, aggregation, migration, proliferation, differentiation, function or combinations thereof that is different from other removable members within the set.

The stiffness of a removable member may be selected to induce cell growth that is different from other removable members within the set.

Each removable member may independently comprise a substrate with a selected stiffness. The substrate may be any material that has a suitable stiffness for culturing cells thereon. The substrate may be a solid, liquid, gas or gel. The substrate may comprise a polymer, metal, wood or any thereof.

Each removable member may independently comprise a polymer substrate. Each removable member may independently comprise a polymer substrate with a selected stiffness.

The stiffness of the polymer substrate may selected to be in the range of about 1 to about 2000 kPa.

The step of providing at least one removable member may comprise the step of selecting the polymer of the polymer substrate from the group consisting of polydimethylsiloxane, polyacrylamide, polyethylene glycol, hyaluronic acid, poly(hydroxyethylmethacrylate) polyethylene glycol, polycaprolactone, polylactic acid, poly(methylmethacrylate), polyacrylonitrile, polyamide, agar, agarose, collagen and any mixture thereof.

The polymer of the polymer substrate may comprise an additive.

The additive may be any material that chemically or physically changes the property of the polymer.

The step of providing at least one removable member may comprise the step of selecting a polymer substrate in a set of polymer substrates that have different stiffness to each other due to additives that confer stiffness on the polymer substrates and in which each polymer substrate of the set has different levels of additives contained therein.

The step of providing at least one removable member may comprise the step of selecting an additive that confers stiffness to the polymer of the polymer substrate. The step of providing at least one removable member may comprise the step of selecting an additive that may confer stiffness to the polymer substrate, the additive selected from the group consisting of dielectric gel, elastomer, curing agent, solvent, pigment, stabilizer, UV stabilizer, heat stabilizer, biostabilizer, antioxidant, surfactant, plasticizer, lubricant, anti-counterfeit, antimicrobial, antistatic agent, blowing agent, filler, extender, flame retardant, process aid, reinforcement and any combination thereof.

The additive may be selected to modulate the stiffness of the polymer of the polymer substrate.

The step of providing at least one removable member may comprise the step of selecting an additive that may confer stiffness to the polymer substrate, the additive selected from the group consisting of dielectric gel, elastomer, curing agent, solvent and any combination thereof.

The step of providing at least one removable member may comprise the step of contacting a dielectric gel and an elastomer in a ratio in the range of about, about 2:1 to about 1:1, about 2:1 to about 1:2, about 2:1 to about 1:5, about 2:1 to about 1:10, about 2:1 to about 1:20, about 1:1 to about 1:2, about 1:1 to about 1:5, about 1:1 to about 1:10, about 1:1 to about 1:20, about 1:2 to about 1:5, about 1:2 to about 1:10, about 1:2 to about 1:20, about 1:5 to about 1:10, about 1:5 to about 1:20 or about 1:10 to about 1:20.

The step of providing at least one removable member may comprise the step of disposing a sacrificial layer of 5% (w/v) sucrose solution on the polymer substrate to reduce adhesion between the chamber and the removable member. The sacrificial layer may be any chemical or solvent that may form a thin layer that reduces adhesion between the silicon wafer and the membrane. The sacrificial layer on the polymer substrate may comprise a liquid selected from the group consisting of sucrose solution, 5% (w/v) sucrose solution, poly(acrylic acid), poly(methyacrylic acid) and dextran solutions. The deposition of the sacrificial layer on the polymer substrate may be performed by spin-coating at a speed in the range of about 1500 RMP to about 4000 RPM for a duration of time in the range of about 10 seconds to about 20 seconds.

The method for fabrication may comprise the step of connecting the chamber with at least one removable member having a selected stiffness. The connecting step may be layering the chamber on top of the at least one removable member. The connecting step may be reversible. That is, the chamber may be disconnected from the at least one removable member.

The method for fabrication may comprise the step of providing a removable lid to enclose the chamber.

The method for fabrication may comprise the step of disposing a liquid layer on the at least one removable member, the liquid selected to reduce adhesion of the removable member to the chamber.

The method for fabrication may comprise the step of providing plural chambers.

A use of a cell culture apparatus, the apparatus comprising at least one chamber for containing and growing the cells therein, the chamber being adapted to connect with at least one removable member of a set of removable members, each of the removable members providing a surface for cell adhesion and having a different stiffness relative to other removable members of the set, the stiffness of a removable member being selected to induce cell growth that is different from other removable members within the set.

A method for measuring the stiffness of an apparatus, the apparatus comprising at least one chamber for containing and growing the cells therein, the chamber being adapted to connect with at least one removable member of a set of removable members, each of the removable members providing a surface for cell adhesion and having a different stiffness relative to other removable members of the set, the stiffness of a removable member being selected to induce cell growth that is different from other removable members within the set.

BRIEF DESCRIPTION OF THE DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 6 comprising FIG. 6A shows the wrinkling and delamination modes of buckling in the thin film on the substrate system; and FIG. 6B shows the critical stresses for wrinkling and buckling delamination for systems with stiffness ratio $E_s/E_f$.

FIG. 8 comprising FIG. 8A is a graph showing cell area versus stiffness of the underlying substrate. FIG. 8B shows F-actin staining for cells seeded on substrates having 3 different stiffnesses for direct versus through membrane cell seeding on PDMS gels. (Bars denoted standard error. n=30).

EXAMPLES

Non-limiting examples of the invention will be further described in greater detail by reference to specific Examples, which should not be construed as in any way limiting the scope of the invention.

Example 1

The Thin Film Construct

Preparation and Characterization of Thin PDMS Membranes

Figure 1:
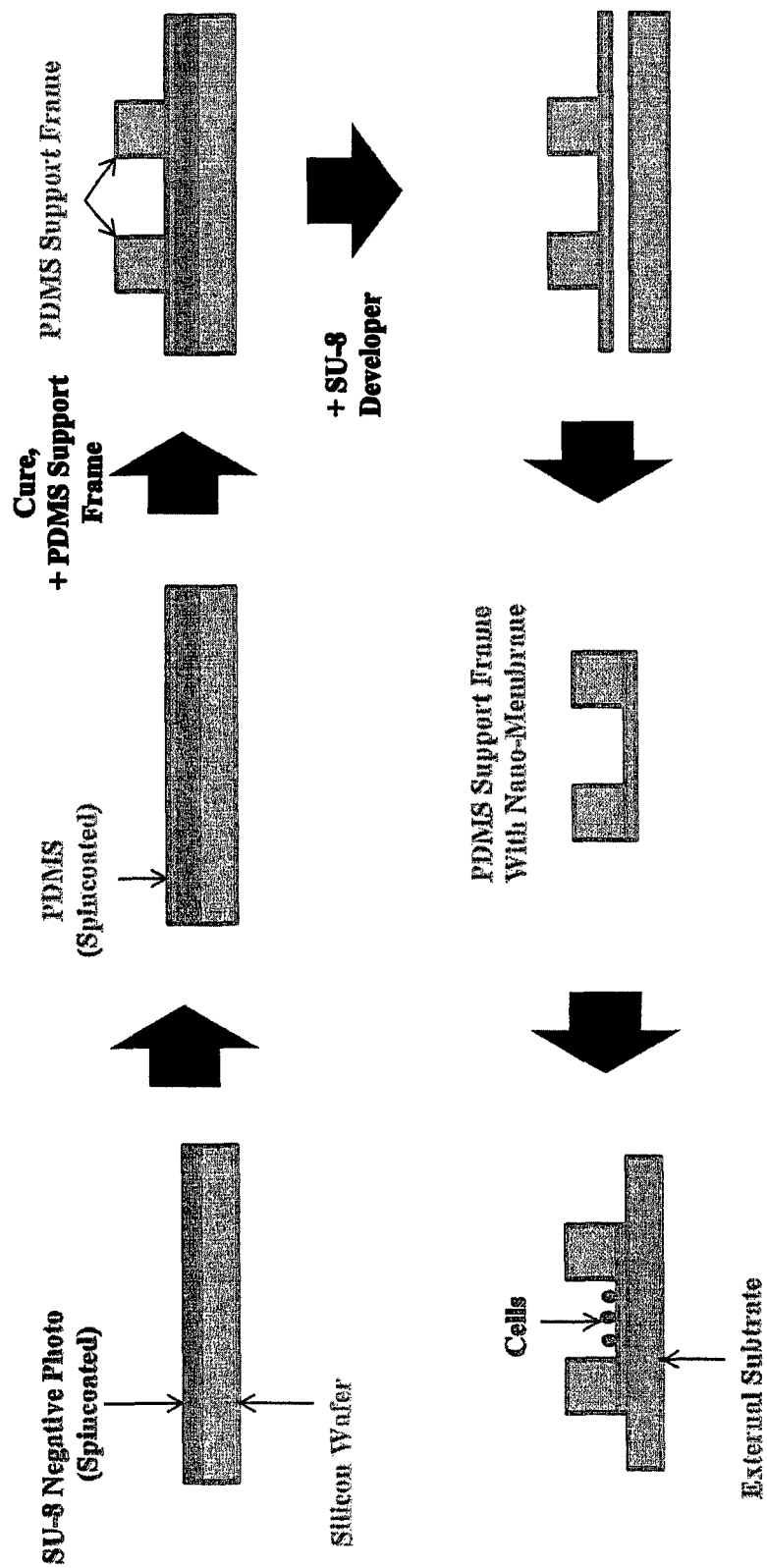
FIG. 1 is a schematic diagram describing one embodiment of the steps involved in the fabrication of thin PDMS membranes attached to PDMS support frames using soft lithography techniques.

By modifying the fabrication process, square thin PDMS membranes with thicknesses from 3 μm down to 100 nm can be fabricated with widths ranging from 100 μm up to 5 mm (FIG. 1). Briefly, SU-8 5 (Micro Chem) was spin-coated onto a silicon wafer. Here, the spin-coating speed and time was optimized to be at 2000 RPM for 30 s respectively. By this step, an even layer of SU-8 5 was obtained, onto which the PDMS membranes were formed.

By varying the base/curing agent ratio in the PDMS membranes (Sylgard 184; Dow Corning), the resulting elastic modulus can be modified. For example, Young's modulus values of 500, 750, 1000, and 1600 kPa were obtained using ratios of 25, 20:1, 15:1, and 10:1 silicone elastomer base/curing agent, respectively.

In order to obtain PDMS membranes with thicknesses in the order of hundreds of nanometers, the PDMS solution can be diluted with hexane (Fisher Scientific) at PDMS:Hexane ratios of 1:5, 1:10, 1:20, 1:30, 1:60 and 1:90 before being spin-coated on top of the SU-8 5 layer at 6000 RPM for 150 s to produce PDMS membranes with 1540, 740, 410, 315, 195 and 96 nm thicknesses respectively.

The silicon wafer construct was baked at 110° C. for 15 min. A thick PDMS square window supporting frame with a height of 3 mm, an outer width of 10 mm and an inner window width of 5 mm was placed onto the PDMS membrane and left to bond at room temperature. To detach the PDMS block with the PDMS membrane bonded to it from the silicon wafer, the silicon wafer construct was placed in an SU-8 developer (Micro Chem) for 1-2 min, and the PDMS block with the PDMS membrane bonded to it was carefully removed and rinsed with ethyl alcohol (95%; PHARMCO-AAPER) and deionized $H_2O$ before being sterilized under the UV hood for 1 hr.

Figure 5:
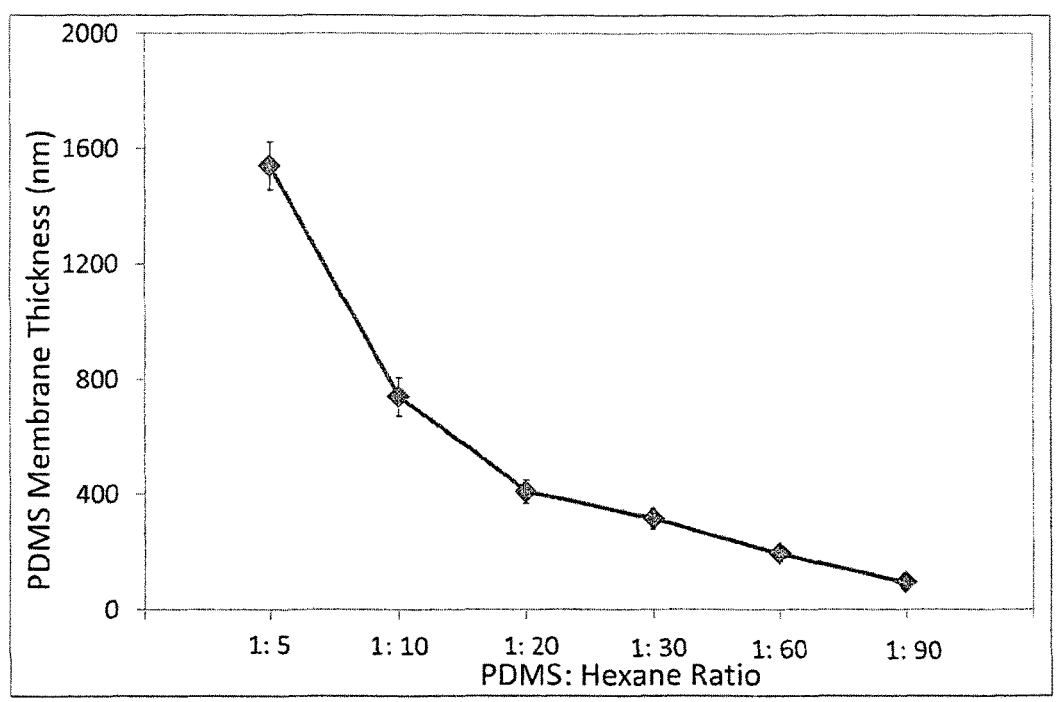
FIG. 5 is a graph showing data on the optimization of thickness for PDMS thin membrane in experiments based on PDMS:Hexane formulation. (Bars denote standard error. n=10).

By varying the PDMS: Hexane ratio, we were able to vary the thickness of the PDMS membranes from 500 nm all the way down to 100 nm (FIG. 5). The thickness of the PDMS membranes were measured using an AFM tapping mode by placing the membrane on a glass cover slip and scratching the membrane to expose the underlying glass. The difference in topographical height between the membrane surface and the glass coverslip surface is the thickness of the membrane.

By using this method of diluting the polymer with a solvent and spin-coating the silicone wafer with a sacrificial layer of SU-8 5, it is possible to fabricate membranes with a thickness in the range of 50 nm to 5 μm also having a large diameter of up to 10 mm.

Preparation of Underlying PDMS Gel Substrates

Commercially available PDMS, Sylgard 527 gel and Sylgard 184 elastomer (Dow Corning), were mixed to create PDMS substrates with different mechanical properties. Sylgard 527 was prepared by mixing equal weights of part A and B while Sylgard 184 was prepared by mixing a 10:1 ratio of silicone elastomer base/curing agent. Three different ratios of the Sylgard 184: Sylgard 527 were evaluated; 1:0, 1:20 and 1:10. Pure Sylgard 527 and Sylgard 184 polymer mixtures were first created separately as described above before being mixed at the three different ratios and degassed under vacuum to remove any bubbles before curing overnight at 60° C. The stiffnesses of the three polymers, as measured using methods known in the art were 5, 20 and 50 kPa for Sylgard 527: Sylgard 184 ratios of 1:0, 1:20 and 1:10 respectively.

To increase the future rate of detachment of the underlying PDMS gel substrate from the PDMS membranes, a sacrificial layer of 5% (w/v) sucrose solution was spin-coated onto the PDMS gel substrates at 3000 RPM for 15 s. The PDMS gel substrate was then baked at 80° C. for 30 min.

Other underlying PDMS gel substrates include formulations of PDMS whereby stiffnesses can be changed either by varying the amount of premixed components before mixing to obtain the final polymeric solution or by varying the amount of curing agent added. In one example, the PDMS polymer CY52-276 (Dow Corning) is used. By mixing and varying the amount of CY52-276A and CY52-276B added to the final polymeric solution to be cured, the stiffness of the PDMS gel can be tuned upwards from a Young's Modulus of 1 kPa.

Figure 2:
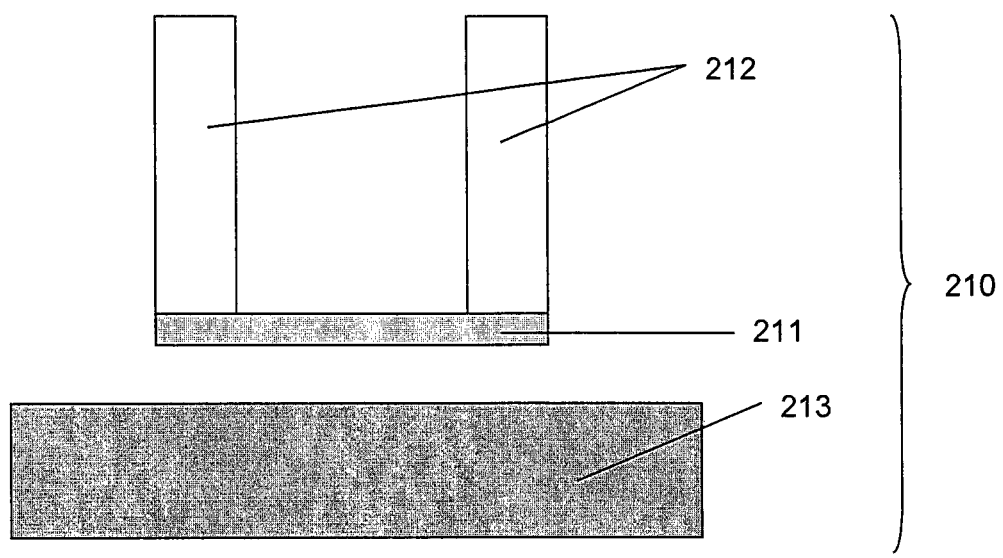
FIG. 2 is a schematic diagram of one embodiment of the apparatus used for dynamic and reversible control of substrate stiffness during cell culture.

FIG. 2 shows a summary of all the components of the containment layer such as a membrane 210 mentioned above. The three components are the thin PDMS membrane construct 211, the support frames 212, and the underlying PDMS gel substrate 213.

Cell Seeding

To prepare PDMS membranes for cell culture, the surfaces were first sterilized using ethyl alcohol (PHARMCO-AAPER). Phosphate-buffered saline (PBS; Fisher Scientific) at a 10× solution was diluted to 1× with deionized $H_2O$, filtered, and used as a buffer solution. The PDMS substrates were coated with fibronectin (10 mg/mL, PBS; BD Biosciences) for 60 min. NIH 3T3 fibroblasts (National Institutes of Health) were washed once with PBS and then exposed to trypsin-ethylenediamine-tetraacetate (0.05%; Invitrogen) for 5 min to dissociate them from the tissue culture plates. The cells were then seeded onto the PDMS membranes and cultured at 37° C. and 5% carbon dioxide in growth media consisting of Dulbecco's modified Eagle's medium supplemented with 10% calf serum, glutamine (0.3 mg/mL), streptomycin (100 mg/mL), penicillin (100 U/mL), and 20 mM n-2-hydroxyethylpiperazine-n'-2-ethanesulfonic acid at a pH of 7.4. Cells were incubated for 24 h to allow them to attach and spread.

Modulation of Stiffness

Figure 3:
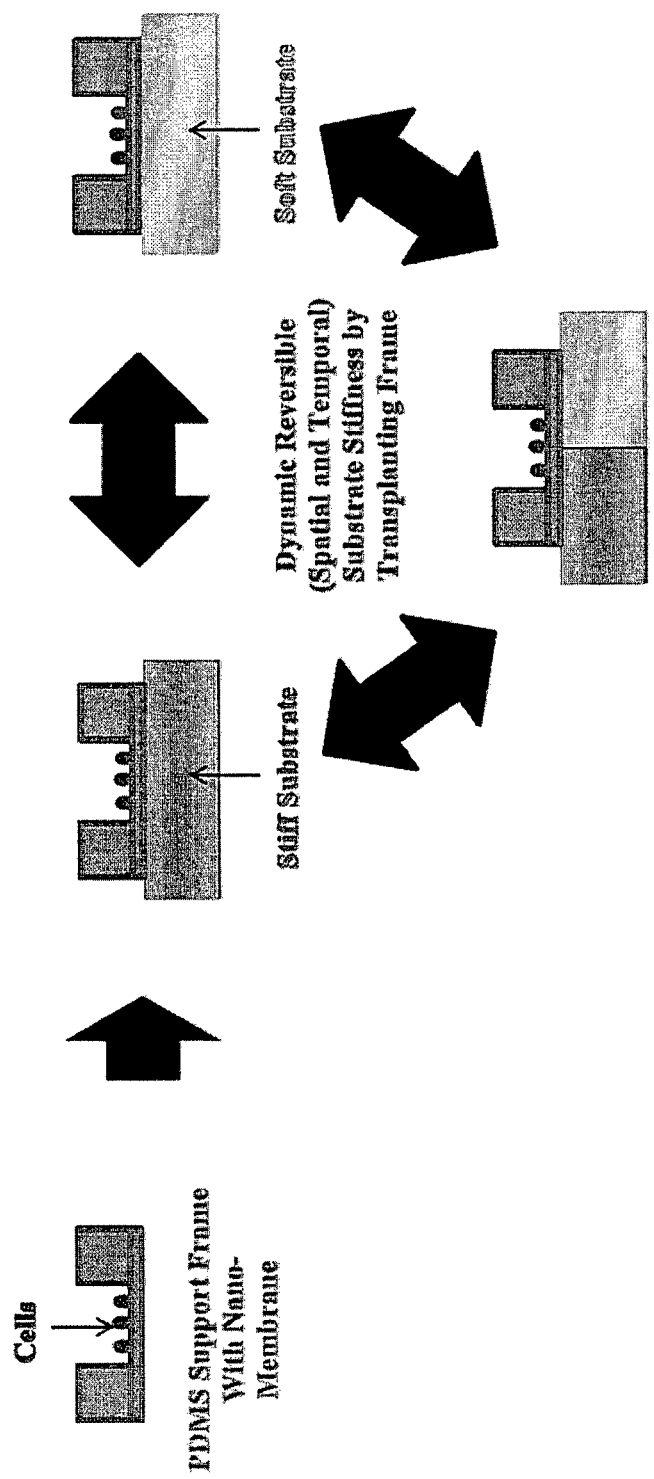
FIG. 3 is a schematic diagram describing one embodiment of the steps involved for spatially and temporally modulating the substrate stiffness both dynamically and reversibly.

The PDMS membranes with cells seeded on them were transplanted between PA gels with differing stiffnesses to simulate a dynamic substrate stiffness environment (FIG. 3). When transplanting, deionized H$_2$O was added in-between the thin-film and the underlying PDMS substrate to reduce adhesion forces between the two layers before they are separated. The temporal stiffening of the cell environment was simulated by transplanting the PDMS membranes from a softer to a stiffer underlying PA substrate and vice versa. The spatial modulation of the substrate stiffness environment was obtained by shifting an underlying hard/soft PA gel substrate interface underneath the PDMS membrane to simulate a spatially changing stiffness environment for the cells on the PDMS membrane.

Specifically, a 1.5 μm thick PDMS thin membrane was first attached to a PDMS upright frame having a 10 mm by 10 mm window and a height of 10 mm. The frame was placed in a UV hood for 1 hr to sterilize it. The frame was then placed onto a removable PDMS underlying substrate with a stiffness of 1 kPa in a 60 mm petri dish. The PDMS underlying substrate was pre-coated with 5% sucrose solution using spin-coating. Next, the thin PDMS membrane was coated with fibronectin (10 mg/mL in PBS) for 60 min. 0.5 ml of an NIH 3T3 cell suspension at a density of 10,000 cells/mL were then seeded onto the PDMS membranes and cultured at 37° C. and in an atmosphere of 5% carbon dioxide in growth media consisting of Dulbecco's modified Eagle's medium supplemented with 10% calf serum, glutamine (0.3 mg/mL), streptomycin (100 mg/mL), penicillin (100 U/mL), and 20 mM n-2-hydroxyethylpiperazine-n0-2-ethanesulfonic acid at a pH of 7.4. Cells were incubated for 24 h to allow them to attach and spread. The cell morphology was then visualized under a microscope, before deionized H$_2$O was added in between the thin PDMS membrane and the underlying PDMS substrate, and the PDMS upright frame attached to the thin membrane was gently detached from the underlying 1 kPa PDMS substrate. The upright frame with the cells was then placed onto a separate removable 40 kPa PDMS substrate coated with a 5% sucrose layer in a 60 mm petri dish and incubated for 6 hrs. The cell morphologies were then visualized under a microscope.

Example 2

High-Throughput Cell Culture Studies

Figure 4:
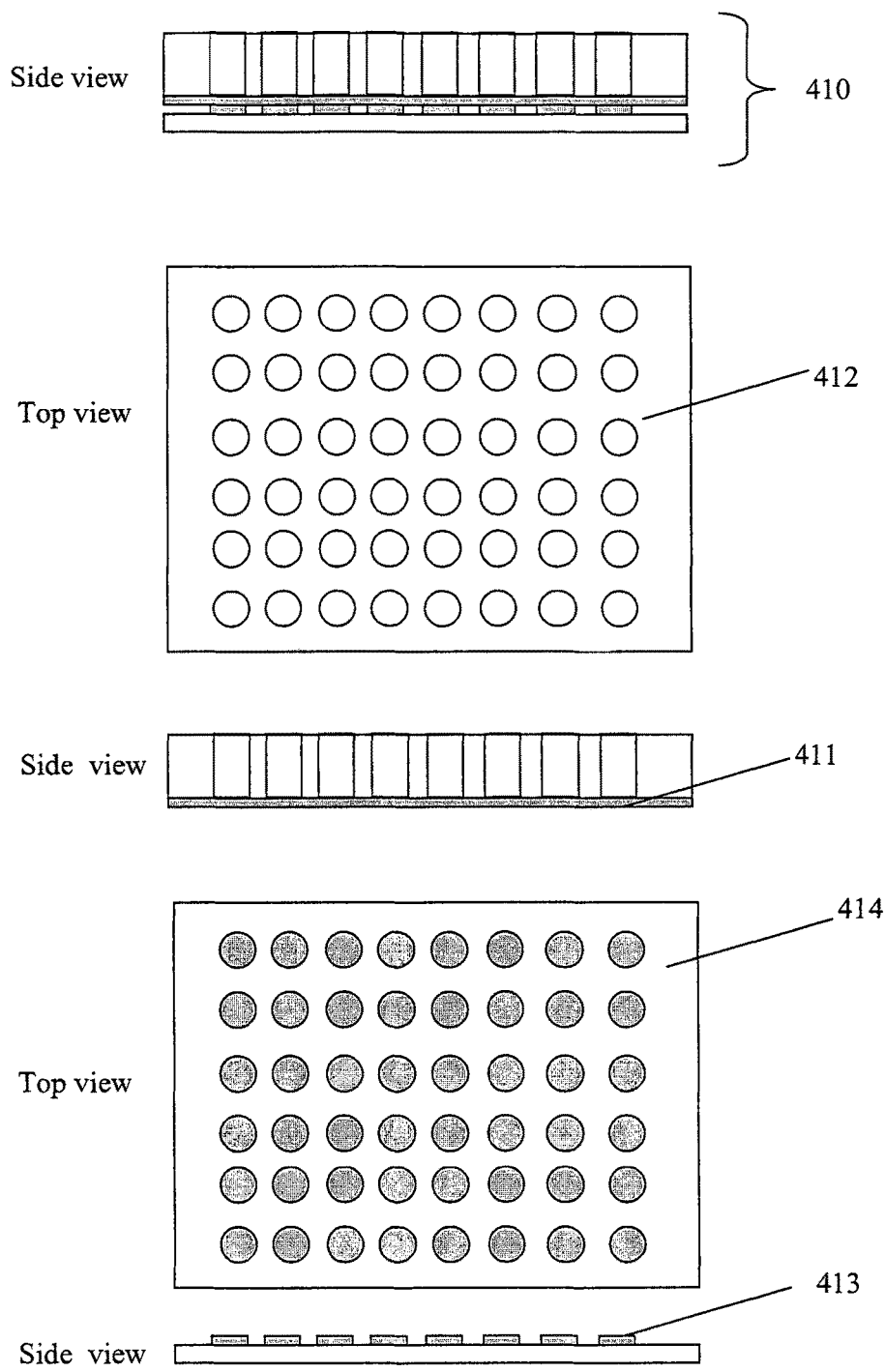
FIG. 4 is a schematic diagram of one embodiment of the apparatus describing a high-throughput example of the apparatus for achieving dynamic and reversible control of substrate stiffness for cell culture.

The description of the above mentioned thin-film construct for cell culture studies can be further expanded to build a high-throughput cell-culture plate assay 410, as shown in FIG. 4. The thin-film 411 is first fabricated as per the previous description, and the support structure used is a bottomless multi-well cell culture plate 412. As such, the bottom of each well would be a thin-film, which is separate from other wells of the plate, allowing for cells in each of the wells to be subjected later to different stiffness conditions. The PDMS gel substrate 413 described previously is patterned onto a large glass coverslip 414, such that the patterns correspond to the shape of the wells in the corresponding multi-well plate 412. The stiffness of the PDMS gel substrate in each circular pattern in 413 can be varied individually. The multi-well component consisting of 411 and 412 can then be placed on top of 413, completing the high-throughput embodiment of the thin-film construct.

Example 3

Methods for Validation of the Thin-Film Construct

Fluorescent Staining and Microscope Visualization

To visualize the cytoskeletal structure of the cells using fluorescent immunostaining, the cells were fixed with 4% paraformaldehyde and treated with 0.1% Triton-X, followed by staining with 6 mM phalloidin-tetramethylrhodamine B isothiocyanate (Sigma-Aldrich) and DAPI (40,6-diamidino-2-phenylindole, dihydrochloride; 2 mg in 1 mL PBS; Invitrogen), which labeled the actin filaments and the nucleus, respectively. After incubating the cells with phalloidin and DAPI, they were mounted on glass coverslips with Fluoromount-G (Southern Biotech). By using an inverted fluorescent microscope (Axiovert 200; Carl Zeiss) with a 63× (1.4 NA) objective, the actin filaments and nucleus of the NIH 3T3 fibroblasts were imaged. Cell sizes and migration speeds were obtained using a 20× (0.3 NA) objective fitted with a temperature control incubator under phase contrast.

Physical Characterization of Stiffness and Thickness

The stiffness of the PDMS gels and the PDMS membrane-PDMS gel, alone or in combination, were determined using a Hertz indentation method through FEA simulations carried out using Autodesk (Autodesk, Inc.). The thicknesses of the PDMS membranes were determined using Atomic Force Microscopy (AFM, Dimension 3000 SPM; Digital Instruments) through surface scanning microscopy.

Data Analysis

Cell areas were measured using a program written in MATLAB (The MathWorks). FEA simulations were carried out using Autodesk (Autodesk, Inc.) and the results were analysed in MATLAB.

Example 4

Delamination

Delamination of the thin PDMS membrane from the underlying PDMS substrate was not observed to occur during cell culture.

Figure 6A:
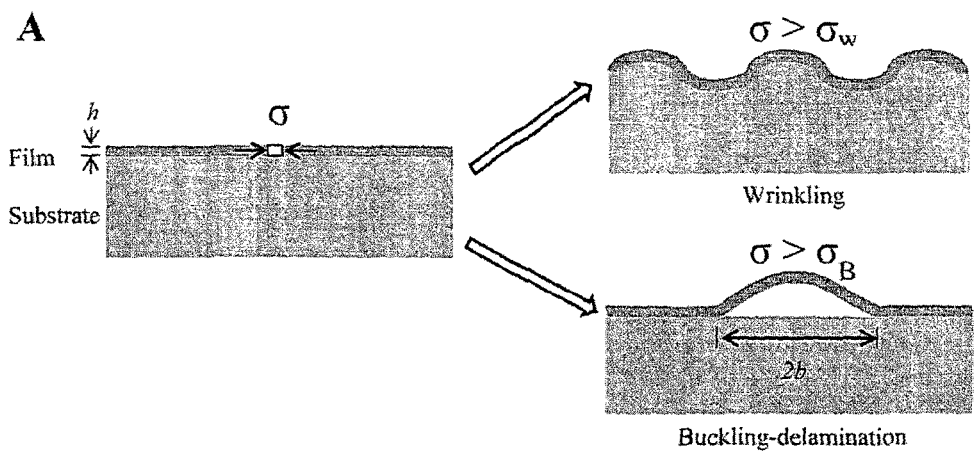
FIG. 6A and FIG. 6B show the effects of wrinkling and buckling delamination of the film.

For an elastic thin film on a compliant substrate, two types of buckling modes can occur due to Compressive stress in the film, σ (FIG. 6A). The first is a buckling of the film without delamination (wrinkling) as shown in FIG. 6A. The critical stress for wrinkling is:

$$\sigma_w = \frac{\overline{E}_f}{4}\left(\frac{3\overline{E}_s}{\overline{E}_f}\right)^{2/3} \quad (1)$$

The plane-strain moduli of the film and substrate are $\overline{E}_f$ and $\overline{E}_s$ respectively. When $\sigma > \sigma_w$, the buckling of the film causes wrinkles to form throughout the surface of the film.

The second mode of buckling for elastic thin films on compliant substrates is the buckling of the film with delamination (buckling-delamination) as shown in FIG. 4A. The critical stress for the buckling of a independent thin film is:

$$\sigma_{B0} = \frac{\pi^2}{12}\left(\frac{h}{b}\right)^2 \overline{E}_f \quad (2)$$

The half width of the delamination and thickness of the film are b and h respectively. On compliant substrates, the critical stress for buckling-delamination of a film on a compliant substrate, $\sigma_B$, can be lower than that of the buckling of a free film $\sigma_{B0}$, depending on how compliant the substrate is. An implicit expression of $\sigma_B$ is:

$$\sqrt{\frac{\sigma_{B0}}{\sigma_B}} \tan\left(\pi \sqrt{\frac{\sigma_B}{\sigma_{B0}}}\right) = \frac{\pi h}{12b}\left(\frac{a_{12}^2}{\frac{b}{h} + a_{11}} - a_{22}\right) \quad (3)$$

Where $a_{11}$, $a_{12}$ and $a_{22}$ are the compliance coefficients of the film-substrate system which are determined numerically through FEA. Equation (3) is then solved semi-analytically using the Newton-Raphson method for $\sigma_B$, using $\sigma_{B0}$ as a first approximation.

Figure 6B:
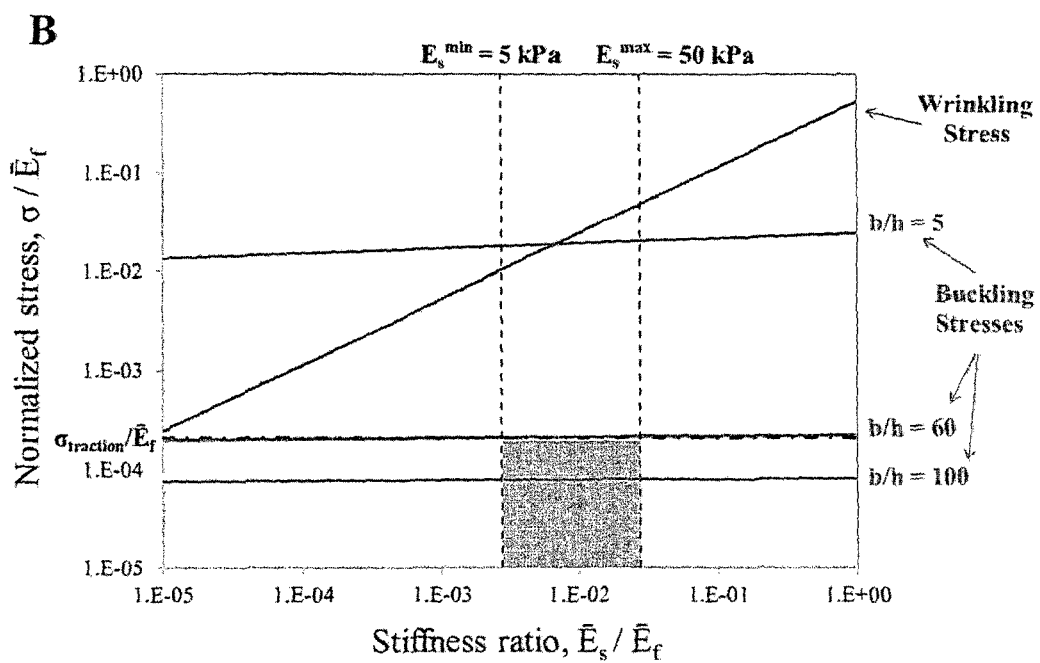

In FIG. 6B, normalized stresses critical stress, $\sigma/E_f$, is plotted against the stiffness ratio $\overline{E}_s/\overline{E}_f$. The plots for wrinkling and buckling delamination for systems with stiffness ratio $\overline{E}_s/\overline{E}_f$ are shown. The critical wrinkling stress (red line) and buckling, stresses associated with b/h ratios of 5, 60 and 100 are plotted. In the present system, a Sylgard 184 PDMS membrane with a young's modulus of $E_s$=1800 kPa was used for all the different film-substrate configurations. For the substrate, the properties of Sylgard 527 PDMS was varied to give three different young's modulus values of $E_f$=5, 20 and 50 kPa. As such, the region of interest (pink area) in the present system as shown in FIG. 1b is then bounded by the dotted vertical lines $E_s^{min}$=5 kPa and $E_s^{max}$=50 kPa and the dotted horizontal line $\sigma_{traction}/E_f$, the known normalized maximum traction force exerted by cells. It can be seen that critical buckling stresses associated with b/h ratios of 60 and above can be experienced in the present system. In order to prevent buckling-delamination from occurring in the present system, a safety factor of 2.5 for the film-substrate system is specified, which translates to satisfying a requirement of b/h≤24.

Example 5

Optimization of PDMS Thin Membrane Thickness

Figure 7:
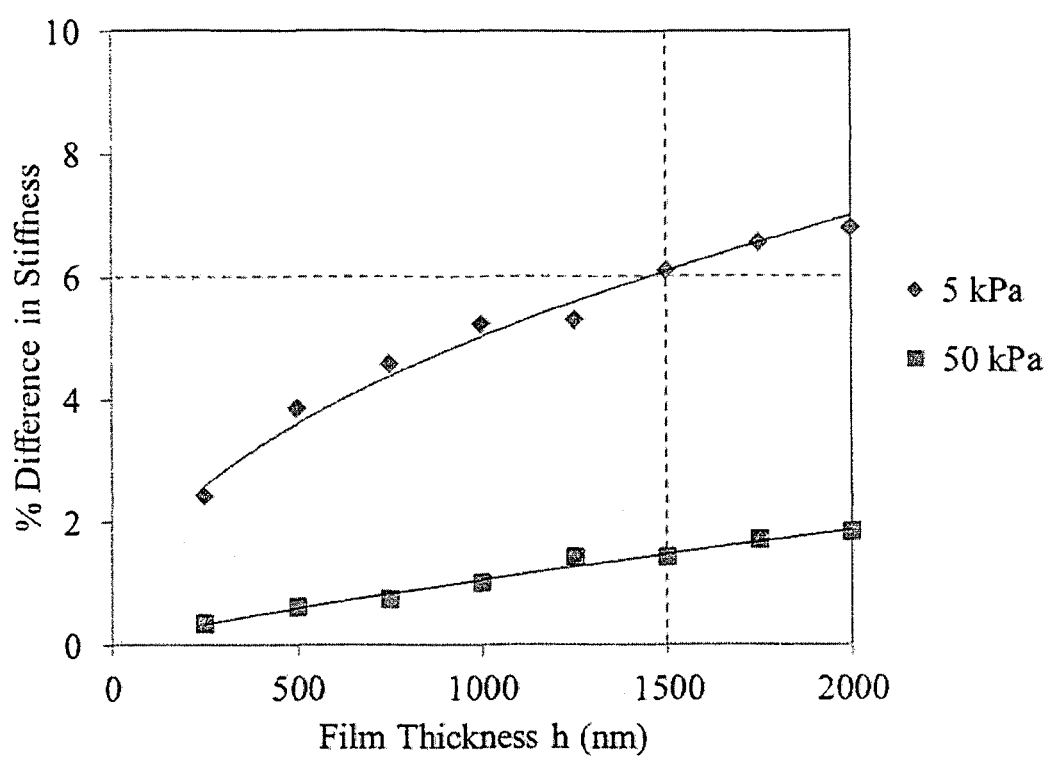
FIG. 7 is a graph showing the percentage difference in stiffness of film-substrate systems, compared to the stiffness of the substrate, measured by Hertz indentation simulated in Autodesk Inventor, plotted against film thickness for film-substrate systems having substrates of 5 kPa and 50 kPa stiffnesses.

Hertz indentation simulations for measuring stiffness were carried out to determine if there were any differences in stiffnesses measured through a PDMS gel as compared to the measured stiffnesses of the underlying PDMS gel alone. These differences between the two cases were quantified as a percentage difference in stiffness between the case where the membrane and the gel are measured together and the case where the gel is measured directly. FIGS. 7, A and B show the FEA simulations of a steel ball before and after indentation into the underlying substrate in Autodesk Inventor.

To fulfill a requirement of b/h≤24 for the present system, b is taken to be bounded and fixed by the maximum radius that a cell can spread on a 2-D substrate (25), which is taken to be 36 Therefore, the only parameter which can be tuned in the present system to satisfy the requirement of b/h≤24 is by increasing h. However, by increasing h, the percentage difference in stiffness of the present film-substrate system compared to the stiffness of the substrate (measured by Hertz indentation) increases, as shown in FIG. 7. A a film thickness of h=1.5 μm was picked, thus settling for a maximum percentage difference in stiffness of approximately 6% for the present experiments.

Having chosen all the appropriate film and substrate parameters, which are film material and thickness, substrate material and range of stiffnesses, the system is configured so not to experience cell traction-induced wrinkling or buckling-delamination, even when transferring the thin film from one underlying substrate to another.

Example 6

Stiffnesses of Substrate and Cell Spread Area

Stiffnesses of substrate and cell spread area using thin-membrane transplantation method were found to be comparable to those seeded directly on the underlying substrate.

Figure 8A:
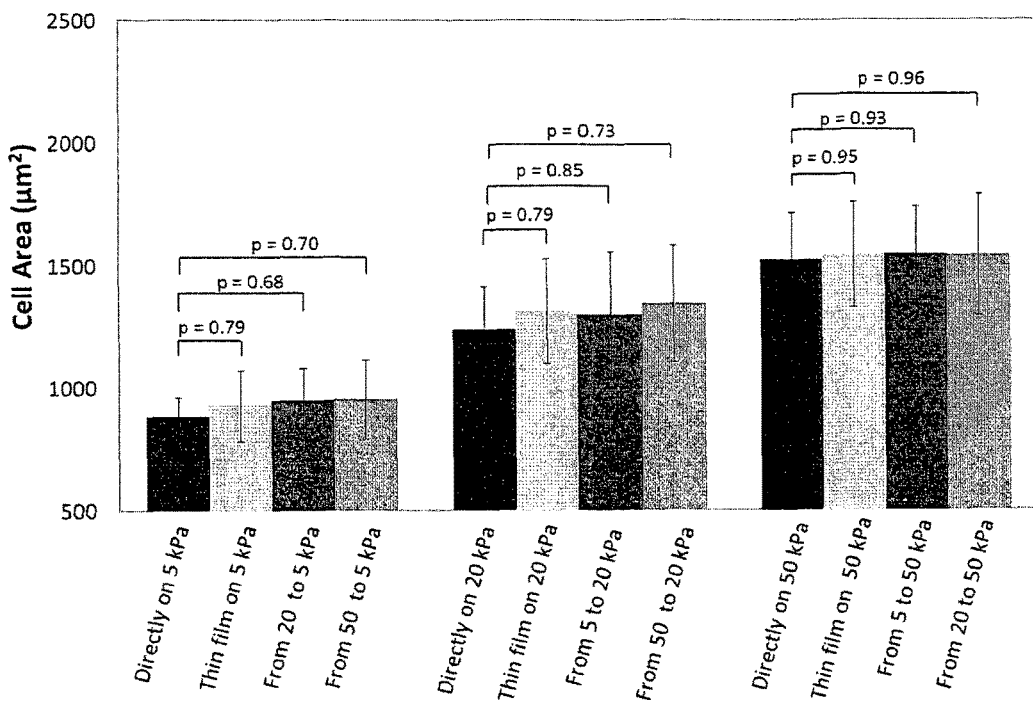
FIG. 8A and FIG. 8B show comparisons between NIH 3T3 cell characteristics when seeded directly onto substrates of different stiffness and when seeded through the thin film-PDMS substrate.

FIG. 8 compares NIH 3T3 cell characteristics seeded directly on 5, 20 and 50 kPa PDMS substrates with cells seeded on the thin film-PDMS substrate construct. FIG. 8A shows a graph of cell area versus stiffness of the underlying substrate. The control cases when cells were seeded directly on the PDMS substrates for 6 hr are shown by the blue bars. The cell spread area of cells in control cases were compared to those of cells seeded on the thin PDMS films, which were placed on substrates of different stiffnesses for 6 hr (denoted by yellow bars), and those of cells seeded on thin PDMS films which were initially placed on PDMS substrates for 6 hr, then transferred to another substrate with a different stiffness than the initial PDMS substrate after 6 hr (denoted by both red and green bars). A student's t-test was conducted on the datasets, using the cell spread area of cells seeded directly on the 5, 20 and 50 kPa PDMS substrates as controls and the p-values of the test are denoted in FIG. 8A. The cell spread area of cells seeded on the thin PDMS films placed on top of underlying PDMS substrates show no significant difference, based on the p-values obtained from the student's t-test at a 90% confidence level ($p<0.1$), when compared to the cell spread area of cells which were seeded directly on top of the PDMS substrates.

When the cells seeded on top of PDMS films are transferred from one PDMS substrate to another with a different stiffness compared to the original, the cell spread area changes and show no significant difference to those seeded directly on the PDMS substrates based on the student's t-test at a 90% confidence level.

Cell spread area of cells seeded on the thin membranes and stuck on top of PDMS gels show no significant differences from those seeded directly on top of PDMS substrates. Even when the films are transplanted from one PDMS substrate to another with different stiffness, the cell spread area changes and show no significant different to those seeded directly on the PDMS substrates. This shows that the membrane overlaid on the PDMS substrate successfully mimics the cell stiffness environment of the PDMS substrate located below the thin PDMS film.

It is noted that the p-values of the cell spread area data groups which were compared to the cell spread area of cells seeded directly on 5 kPa PDMS substrates where on average lower than the p-values of the cell spread area data groups which were compared to the cell spread area of cells seeded directly on 20 and 50 kPa PDMS substrates respectively, as shown in FIG. 8A. This means that for cells seeded on the thin PDMS films which were placed on the 50 kPa underlying PDMS substrates, their cell spread area more closely resembled those of cells seeded directly on the 50 kPa PDMS substrates. A reason for this could be that the difference in stiffness of the membrane overlaid on the PDMS substrate (for thin PDMS films on underlying PDMS substrates) as compared to the stiffness of the underlying PDMS substrates were lower for 50 kPa PDMS substrates than for 5 kPa PDMS substrates, as shown previously in FIG. 7C. Since cell spread area is known to increase with substrate stiffness, this could explain why cells seeded on the thin PDMS films which were placed on the 50 kPa underlying PDMS substrates had cell spread areas more closely resembled those of cells seeded directly on the 50 kPa PDMS substrates as compared to the 20 and 5 kPa PDMS substrates.

Figure 8B:
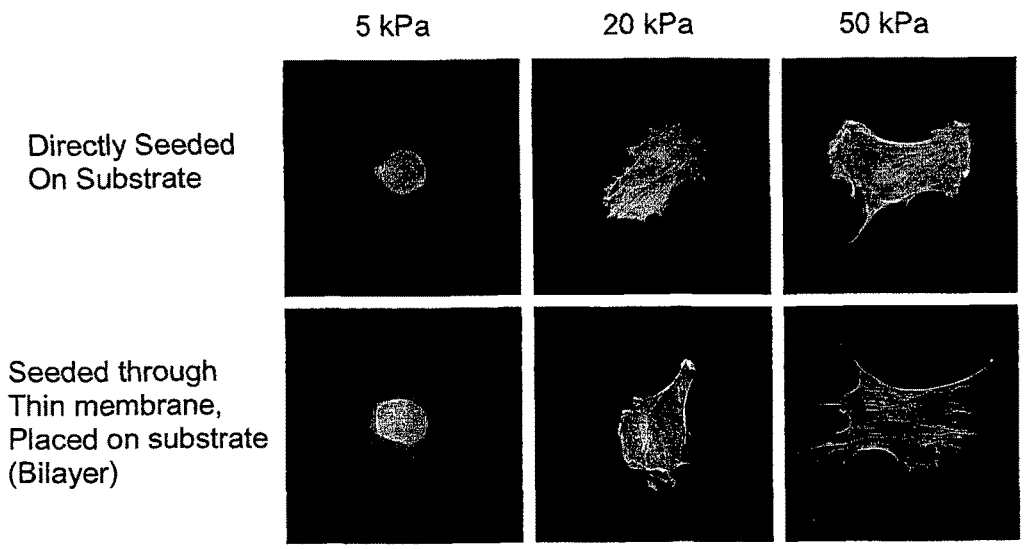

The F-actin structures of cells stained with Alexa-Phallodin for cells seeded on thin PDMS membrane-PDMS substrate constructs compared to cells seeded directly on 3 PDMS substrates with differing stiffnesses (1, 20 and 50 kPa) are shown in FIG. 8B. Stress fibers become more prominent in both cases where the stiffness of the underlying substrates are increased, further demonstrating that the cells can sense the stiffness of their underlying substrate layer below the PDMS membrane.

The present invention has been described in accordance with several examples, which are intended to be illustrative in all aspects rather than restrictive. Thus, the present invention is capable of many variations in detailed implementation, which may be derived from the description contained herein by a person of ordinary skill in the art.

APPLICATIONS

The apparatus and method may be used to investigate the influence of reversible dynamic stiffness environments on cell morphology, motility, proliferation and differentiation in various cells types.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A cell culture apparatus for culturing cells, the apparatus comprising:
   at least one chamber for containing and growing the cells therein; and
   a set of removable members, each of the removable members of said set providing a surface for cell adhesion and having a different stiffness relative to other removable members of the set, the stiffness of each removable member of said set being selected to induce cell growth that is different from other removable members within the set,
   wherein the at least one chamber being adapted to connect with at least one removable member of the set of removable members,
   wherein at least one removable member of the set of removable members is removably connected to the at least one chamber, and
   wherein the at least one chamber comprises at least one containment layer for containing cells within the chamber during cell culture, the containment layer disposed between the interior of the chamber and the surface for cell adhesion of the removable member connected to the chamber.

2. The apparatus of claim 1, wherein the containment layer is dimensioned to enable cell growth to be affected by the surface for cell adhesion of the removable member.

3. The apparatus of claim 2, wherein the containment layer comprises a polymer membrane.

4. The apparatus of claim 3, wherein the polymer membrane comprises a polymer sheet disposed between sidewalls of the chamber and the surface for cell adhesion of the removable member.

5. The apparatus of claim 3, wherein the polymer membrane has a thickness in the range of 50 nm to 5 μm.

6. The apparatus according to claim 1, wherein each removable member independently comprises a polymer substrate.

7. The apparatus according to claim 6, wherein the stiffness of each polymer substrate of said set is selected to be different due to the presence of different amounts of one or more additives that confer stiffness on the polymer substrates.

8. The apparatus according to claim 7, wherein the one or more additives that confers stiffness to the polymer substrate is selected from the group consisting of dielectric gel, elastomer, curing agent, solvent and any combination thereof.

9. The apparatus according to claim 8, wherein the polymer substrate comprises dielectric gel and elastomer in a ratio in the range of 2:1 to 1:20.

10. The apparatus according to claim 1, comprising a liquid layer disposed between the removable member and the containment layer for reducing adhesion of the removable member to the containment layer.

11. The apparatus according to claim 1, wherein the chamber is capable of being connected to plural removable members simultaneously during cell growth.

12. The apparatus according to claim 1, comprising plural chambers.

13. The apparatus according to claim 12, wherein multiple removable members are configured to interact with multiple chambers so that cells contained within the containment layer of each chamber are able to be contacted with the multiple removable members during cell growth.

14. A cell culture kit for culturing cells having different growth characteristics, the kit comprising:
   at least one chamber for containing and growing the cells therein; and
   a set of removable members, each of the removable members of said set providing a surface for cell adhesion and having a different stiffness relative to other removable members of the set, the stiffness of each removable member of said set being selected to induce cell growth that is different from other removable members within the set,
   wherein the at least one chamber being adapted to connect with at least one removable member of the set of removable members,
   wherein at least one removable member of the set of removable members is adapted to removably connect to the at least one chamber, and
   wherein the at least one chamber comprises at least one containment layer for containing cells within the chamber during cell culture, the containment layer disposed between the interior of the chamber and the surface for cell adhesion of the removable member adapted to connect to the chamber.

15. The cell culture kit of claim 14, wherein the containment layer is dimensioned to enable cell growth to be affected by the surface for cell adhesion of the removable member.

16. The cell culture kit of claim 15, wherein the containment layer comprises a polymer membrane.

17. The apparatus of claim 16, wherein the polymer membrane has a thickness in the range of 50 nm to 5 μm.

18. The cell culture kit according to claim 14, wherein each removable member independently comprises a polymer substrate.

19. The cell culture kit according to claim 18, wherein the stiffness of each polymer substrate of said set is selected to be different due to the presence of different amounts of one or more additives that confer stiffness on the polymer substrates.

20. The cell culture kit according to claim 19, wherein the one or more additives that confers stiffness to the polymer substrate is selected from the group consisting of dielectric gel, elastomer, curing agent, solvent and any combination thereof.

21. The cell culture kit according to claim 20, wherein the polymer substrate comprises dielectric gel and elastomer in a ratio in the range of 2:1 to 1:20.

22. The cell culture kit according to claim 14, wherein the chamber is capable of being connected to plural removable members simultaneously during cell growth.

23. The cell culture kit according to claim 14, comprising plural chambers.

24. The cell culture kit according to claim 23, wherein multiple removable members are configured to interact with multiple chambers so that cells contained within the containment layer of each chamber are able to be contacted with the multiple removable members during cell growth.

25. A method for culturing cells in a cell culture apparatus, wherein the cell culture apparatus comprises:
at least one chamber for containing and growing the cells therein; and
a set of removable members, each of the removable members of said set providing a surface for cell adhesion and having a different stiffness relative to other removable members of the set, the stiffness of each removable member of said set being selected to induce cell growth that is different from other removable members within the set,
wherein the at least one chamber being adapted to connect with at least one removable member of the set of removable members,
wherein at least one removable member of the set of removable members is removably connected to the at least one chamber, and
wherein the at least one chamber comprises at least one containment layer for containing cells within the chamber during cell culture, the containment layer disposed between the interior of the chamber and the surface for cell adhesion of the removable member connected to the chamber;
the method comprising steps of:
selecting a removable member from the set of removable members,
connecting the at least one chamber to the removable member,
culturing cells in the at least one chamber,
consecutively disconnecting the at least one chamber from the removable member and
connecting the at least one chamber to another removable member selected from the set of removable members.

* * * * *